United States Patent
Skinner et al.

(10) Patent No.: US 6,605,472 B1
(45) Date of Patent: Aug. 12, 2003

(54) MICROFLUIDIC DEVICES CONNECTED TO GLASS CAPILLARIES WITH MINIMAL DEAD VOLUME

(75) Inventors: Cameron Skinner, Edmonton (CA); Thompson Tang, Edmonton (CA); D. Jed Harrison, Edmonton (CA); Nicolas Bings, Bloomington, IN (US); Can Wang, Edmonton (CA); Gregor Ocvirk, Edmonton (CA); Jianjun Li, Hull (CA); Pierre Thibault, Aylmer (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/169,146

(22) Filed: Oct. 9, 1998

(51) Int. Cl.[7] .......................... G01N 33/00; G01N 27/27; B01D 59/44

(52) U.S. Cl. ........................ 436/171; 239/690; 250/288; 204/601; 204/604; 436/86; 436/87; 436/88; 436/89; 436/90; 436/91; 436/93; 436/94; 436/173; 436/174; 436/177; 436/178; 436/180

(58) Field of Search .................. 204/451, 453, 204/545, 601, 604; 250/281, 288; 239/690; 436/86–90, 93–94, 171, 173, 174, 177, 178, 180

(56) References Cited

U.S. PATENT DOCUMENTS

| | | | | |
|---|---|---|---|---|
| 2,156,156 A | * | 4/1939 | Mahick | 205/766 |
| 3,538,744 A | * | 11/1970 | Karasek | 73/23.1 |
| 3,740,158 A | * | 6/1973 | Bellinger et al. | 356/246 |
| 3,831,618 A | * | 8/1974 | Liston | 137/154 |
| 3,867,042 A | * | 2/1975 | Mayer et al. | 356/246 |
| 4,008,736 A | * | 2/1977 | Wittmann-Liebold et al. | 137/606 |
| 4,052,132 A | | 10/1977 | Oates | 408/1 |
| 4,351,189 A | * | 9/1982 | Gray et al. | 73/196 |
| 4,394,263 A | | 7/1983 | Dosch et al. | 210/198.2 |
| 4,883,760 A | * | 11/1989 | Heelies | 435/296 |
| 4,908,112 A | * | 3/1990 | Pace | 204/299 R |
| 5,132,012 A | * | 7/1992 | Miura et al. | 210/198.2 |
| 5,540,464 A | * | 7/1996 | Picha | 285/328 |
| 5,744,100 A | | 4/1998 | Krstanovic | 422/103 |
| 5,779,868 A | * | 7/1998 | Parce et al. | 204/604 |
| 5,969,353 A | * | 10/1999 | Hsien | 250/288 |

FOREIGN PATENT DOCUMENTS

| | | | |
|---|---|---|---|
| DE | 2621895 | * 12/1977 | |
| EP | 125492 | * 11/1984 | |
| EP | 0 400 377 | 12/1990 | G02B/6/38 |
| GB | 1188356 | * 4/1970 | |
| WO | WO97/04297 | 6/1997 | G01N/1/14 |
| WO | 98/10122 | * 3/1998 | |

OTHER PUBLICATIONS

S. Sorge et al, Sens. Actuators 1997, A63, 191–195.*
J. N. van der Moolen et al, Anal. Chem. 1997, 69, 4220–4225, Oct. 1997.*
O. Niwa et al, Anal. Sci. 1998, 14, 947–953, Oct. 1998.*

(List continued on next page.)

Primary Examiner—Arlen Soderquist
(74) Attorney, Agent, or Firm—Bereskin & Parr

(57) ABSTRACT

A method is provided for joining a microchip device to a capillary tube. The microchip device has a capillary channel opening onto an edge surface of the device. A short hole is drilled into the edge surface, aligned with the capillary channel. The drilling is done with a flat bottom, preferably by a two-step drilling process. Then, the end of the capillary can be inserted into the hole so that its end is substantially flush with the flat bottom of the hole, thereby eliminating dead volume. Testing has shown that this connection provides very little band broadening of samples transported through the capillary channel into the capillary tube. The tip of the capillary tube can be tapered, so that it is suitable for use as an electrospray source for a mass spectrometer.

15 Claims, 8 Drawing Sheets

OTHER PUBLICATIONS

D. W. Matson et al, Proc. SPIE—Int. Soc. Opt. Eng. 1998, 3519, 200–207, Nov. 1998.*

S. Pleasance et al. J. Chromatogr. 1992, 591, 325–339.*

M. S. Kriger et al. Anal. Chem. 1995, 67, 385–389, Jan. 1995.*

G. A. Valaskovic et al. Anal. Chem. 1995, 67, 3802–3805, Oct. 1995.*

J. F. Kelly et al. Anal. Chem. 1997, 69, 51–60, Jan. 1997.*

Q. Xue et al. Anal. Chem. 1997, 69, 426–430, Feb. 1997.*

H. Nakanishi et al. Proc.—IEEE Annu. Int. Workshop Micro Electro Mech. Syst., 10th, 1997, 619–12, 299–304.*

D. Figeys et al. Anal. Chem. 1997, 69, 3153–3160, Aug. 1997.*

C. L. Coyler et al. Electrophoresis 1997, 18, 1733–1741, Sep. 1997.*

N. Xu et al. Anal. Chem. 1998, 70, 3553–3556, Sep. 1998.*

D. Figeys et al. Anal. Chem. 1998, 70, 3721–3727, Sep. 1998.*

N. H. Bings et al. Anal. Chem. 1999, 71, 3292–3296, Aug. 1999.*

EP Patent Abstracts of Japan, Publication No. 62028664, Publication Date Jun. 2, 1987.

"High Performance Liquid Chromatography Partially Integrated onto a Silicon Chip"—Research Articles AMI, 1995, G. Ocvirk et al. 74–82.

"Novel Microstructures and Technologies Applied in Chemical Analysis Techniques"—Mesa—Transducers '97—1997 International Conference on Solid–State Sensors and Actuators pp. 511–514, V. L. Spiering et al.

"Optimization of Confocal Epifluorescence Microscopy For Microchip–Based Miniaturized Total Analysis Systems"—The Analyst, Jul. 1998, vol. 123 (pp. 1429–1434), G. Ocvirk et al.

"Correlation Capillary Zone Electrophoresis, a Novel Technique to Decrease Detection Limits"—Chromatographia vol. 40, No. 7/8, Apr. 1995 (pp. 368–374), J.N. van der Moolen et al.

"Chemical Amplification Continuous–Flow PCR on a Chip"—Science, vol. 280, May 15, 1998 (pp. 1046–1048), M. U. Kopp et al.

"A Microdevice with Integrated Liquid Junction For Facile Peptide and Protein Analysis by Capillary Electrophoresis/Electrospray Mass Spectrometry"—Analytical Chemistry, vol. 72, No. 5, Mar. 1, 2000 (pp. 1015–1022), B. Zhang et al.

"Microfabricated Devices for Capillary Electrophoresis—Electrospray Mass Spectrometry"—Analytical Chemistry, vol. 71, No. 15, Aug. 1, 1999 (pp. 3258–3264), B. Zhang et al.

"Integrated Multichannel Microchip Electrospray Ionization Mass Spectrometry: Analysis of Peptides From On–Chip Tryptic Digestion of Melittin"—Rapid Communication In Mass Spectrometry, vol. 11, (pp. 1253–1256) (1997), Q. Xue et al.

"A Micromachined Chip–Based Electrospray Source for Mass Spectrometry"—Analytical Chemistry, vol. 72, No. 2, Jan. 15, 2000 (pp. 367–375), L. Licklider et al.

"An Integrated Microfluidics–Tandem Mass Spectrometry System for Automated Protein Analysis"—Analytical Chemistry, vol. 70, No. 18, Sep. 15, 1998 (pp. 3728–3734), D. Figeys et al.

"Microfabricated Polymer Devices for Automated Sample Delivery of Peptides for Analysis by Electrospray Ionization Tandem Mass Spectrometry"—Analytical Chemistry, vol. 71, No. 20, Oct. 15, 1999 (pp. 4437–4444),T.H. Chan et al.

"Microfabricated Device Coupled with an Electrospray Ionization Quadrupole Time–of–Flight Mass Spectrometer: Protein Identifications Based on Enhanced–resolution Mass Spectrometry and Tandem Mass Spectrometry Data"—Rapid Communications In Mass Spectrometry vol. 12 (pp. 1435–1444) (1998), D. Figeys et al.

"An Integrated Microfabricated Device for Dual Microdialysis and On–Line EST–Ion Trap Mass Spectrometry for Analysis of Complex Biological Samples"—Analytical Chemistry, vol. 71, No. 8, Apr. 15, 1999 (pp. 1485–1490), F. Xiang et al.

"Microfabricated Isoelectric Focusing Device for Direct Electrospray Ionization–Mass Spectrometry"—Electrophoresis 2000, vol. 21, (pp. 191–197), J. Wen et al.

"Subattomole–Sensitivity Microchip Nanoelectrospray Source With Time–Of–Flight Mass Spectrometry Detection"—Anayltical Chemistry, vol. 71, No. 17, Sep. 1, 1999 (pp. 3627–3631), I.M. Lazar et al.

"Generating Electrospray From Microchip Devices Using Electroosmotic Pumping"—Analytical Chemistry, vol. 69, No. 6, Mar. 15, 1997 (pp. 1174–1178), R.S. Ramsey et al.

"Separation and Identification of Peptides From Gel–Isolated Membrane Proteins Using a Microfabricated Device for Combined Capillary Electrophoresis/Nanoelectrospray Mass Spectrometry"—Analytical Chemistry, vol. 72, No. 3, Feb. 1, 2000 (pp. 599–609), J. Li et al.

"Integration of Microfabricated Devices to Capillary Electrophoresis–Electrospray Mass Spectrometry Using a Low Dead Volume Connection: Application to Rapid Analyses of Proteolytic Digests"—Analytical Chemistry, vol. 71, No. 15, Aug. 1, 1999 (pp. 3036–3045), J. Li et al.

"Rapid and Sensitive Separation of Trace Level Protein Digests Using Microfabricated Devices Coupled to a Quadrupole–Time–of–Flight Mass Spectrometer"—Electrophoresis 2000, vol. 21 (pp. 198–210), J. Li et al.

* cited by examiner

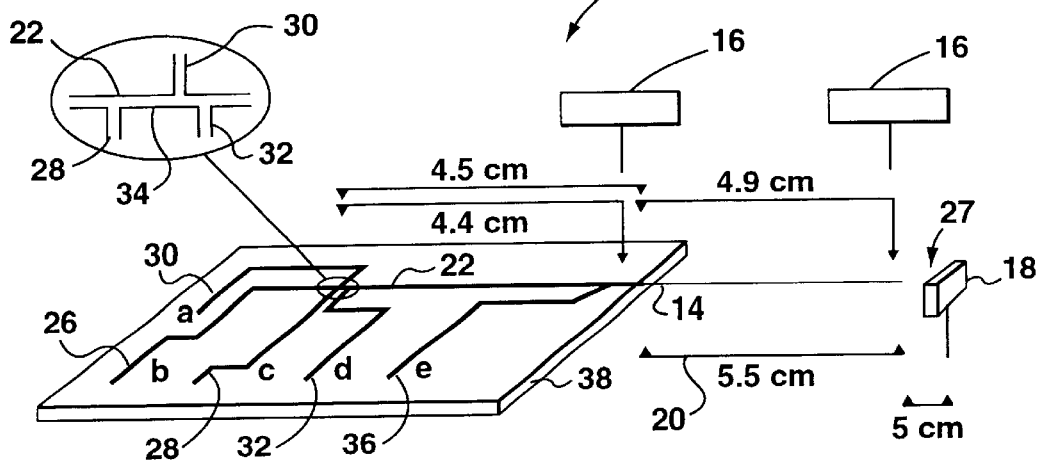
FIG. 1a
FIG. 1
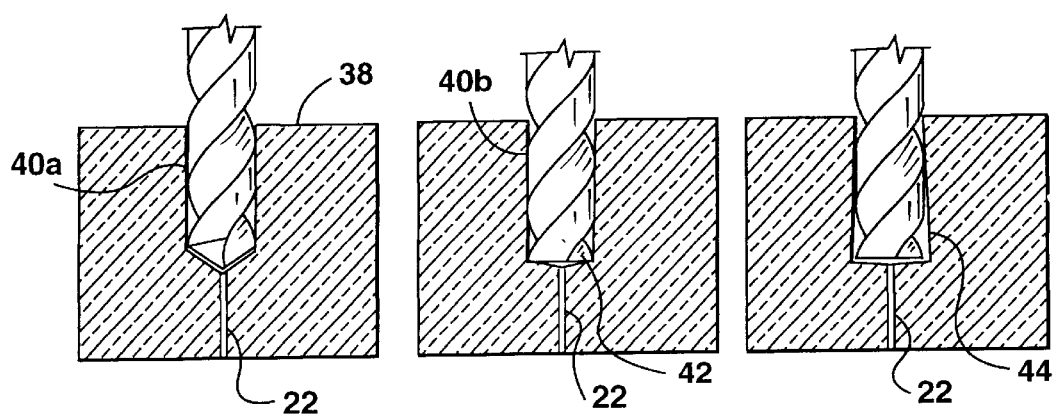
FIG. 3a  FIG. 3b  FIG. 3c

MICROFLUIDIC DEVICES CONNECTED TO GLASS CAPILLARIES WITH MINIMAL DEAD VOLUME

FIELD OF THE INVENTION

This invention relates to microfluidic devices, and more particularly, relates to an apparatus for and a method of coupling a microfluidic device to an electrospray or other interface of a mass spectrometer.

BACKGROUND OF THE INVENTION

Glass microfluidic devices have shown their vast potential in the field of analytical chemistry in the last decade and enable a certain amount of separation and analysis to be carried out. However, to augment the analytical capabilities of microfluidic chip systems, it is necessary to couple these devices to other instruments, and in particular it is desirable to be able to couple them to mass spectrometers. Other uses for this type of connection include, but are not limited to, coupling of the microfluidic device to conventional Capillary Electrophoresis (CE) detectors, sample introduction to a device, automation of a device and interconnections between devices. In large part, these microfluidic devices find their greatest utility in high performance separations. Therefore, connections to the devices must have minimal dead volumes so that the efficiency of the system is not compromised.

The coupling of separation methods with mass spectrometry provides a powerful tool for rapid identification of target analytes present at picogram levels in biological matrices, and structural characterization of complex biomolecules ranging from small pharmaceuticals to complex antibodies. Furthermore, mass spectrometry using electrospray ionization (ESMS) has emerged as a sensitive technique in a number of applications including the sequencing of peptides comprising common or modified amino acids, and the analysis of short DNA oligomers. Further modification of ESMS has improved sensitivity substantially through the use of ionization techniques operating at sub-microliter flow rates, giving $\mu$ESMS. The flow rates used and potentials applied in $\mu$ESMS are compatible with CE, and this has led to development of CE-$\mu$ESMS instruments, capable of initial separations followed by mass spectral analysis. A drawback of this approach is the 15–40 min. seperation on times often required, which tends to underutilize the spectrometer.

Microchip technology has recently been applied to CE, generating an extremely powerful separation and sample pretreatment tool (chip-CE) with analysis time of a few seconds. Separations have been combined on-chip with sample dilution, derivatization, enzyme digestion, and a set of independent manifolds for separation have been integrated on to a single chip to give a form of multiplexed analysis. Thus, sample pretreatment can be automated within an integrated device, a feature which could offer significant advantages in sample preparation for mass spectrometry, particularly if the chip could be designed as an ion source within an ESMS system.

Mass spectrometry using electrospray ionization has emerged as a sensitive technique, providing peptide analysis in the low nanogram range for digested protein using sequence tags and data base searching (Mann, M., Wilm, M., *Anal. Chem.*, 66, 4390–4399 (1994)). Sequence information can be obtained from tandem mass spectrometric analysis where a given multiply-charged precursor ion is selected by the first mass analyzer and the fragment ions resulting from collisional activation with a neutral target gas (e.g. Argon) are transmitted into the second mass analyzer. The product ion spectra are characterized by easily identifiable series of fragment ions, and can be interpreted in the absence of protein or DNA sequence. Even in situations where only partial sequence is obtained, the sequence tag plus the peptide molecular weight can be used to locate the peptide in a given protein or data base. This combined approach was recently presented for the characterization of proteins from silver-stained polyacrylamide gels (Shevchenko, A., Wilm, M., Vorm, O., Mann, M.,*Anal. Chem.*, 68, 850–858 (1996)). Such advances have been facilitated by the introduction of micro-electrospray ionization operating in the low nL/min flow rate regime (Wilm. M. Mann, M., *Int. J. Mass Spectrom. Ion Proc.*, 136, 167–180 (1994)). Although this mode of sample introduction does not require any prior analyte separation (e.g. Liquid chromatography or CE), the sensitivity of the micro-electrospray technique can be adversely affected by the presence of salts used in proteolytic digestion or by the simultaneous ionization of a large number of different peptides isolated from digestion or by the simultaneous ionization of a large number of different peptides isolated from these digests. In addition, the mass spectra of unseparated digests are further complicated by the appearance of multiply-protonated molecules $(M+nH)^{n+}$ for each peptide, which significantly compromise interpretation if more than one peptide is initially present. The combination of a high resolution separation technique to micro-electrospray sources thus confers a unique advantage in situations where both sensitivity and selectivity are desired.

The production of stable ionization conditions from micro-electrospray sources requires critical adjustment of low liquid flow rate (10–300 nL/min), column diameter, and field strength at the micro-electrospray tip. Consequently, the coupling of separation techniques to micro-electrospray is best achieved using CE, which typically operates in a flow rate regime of less than 300 nL/min. Recent reports have demonstrated the applicability of the capillary electrophoresis-micro-electrospray mass spectrometry (CE-$\mu$ESMS) approach for peptides and protein digests (Wahl, J. H., Gale, D. C., Smith, R. D., *J. Chromatogr*, 659, 217–222 (1994); Kriger, M. S., Cook, K. D., Ramsey, R. S., *Anal. Chem.;* 67, 385–389 (1995); Kelly, J. F., Ramaley, L. R.,Thibault, P., *Anal. Chem.* 69, 51–60 (1997)). As a result of the high separation efficiencies obtainable with CE, analyses conducted using CE-$\mu$ESMS typically yield 20–100 femtomoles mass detection limits in full-mass scan acquisition mode and 100–200 femtomoles for tandem mass spectrometric analyses. This is a 10-fold enhancement of sensitivity compared to more conventional (i.e. non-micro) CE-ESMS interface, using a coaxial sheath design operating at flow rates of 2–10 $\mu$L/min.

The limited sample volume used in CZE (2% of capillary volume), results in concentration detection limits of approximately 1 $\mu$M, even at 20 femtomole mass detection limits. Improvement in sample loadings can be achieved using isotachophoretic preconcentration (Foret, F., Szoko, E., Karger, B. L., *J. Chromatogr*, 608, 3 (1992); Foret, F., Sustacek, V., Bocek, P., *J. Microcol. Sep.*, 2, 127 (1990); Mazereeuw, M., Tjaden, U. R., Reinhoud, N.J., *J. Chromatogr. Sc.*, 33, 686 (1995)). This approach was successfully applied to the analysis of paralytic shellfish poisoning toxins present at low nM concentration levels in contaminated shellfish tissues, and enabled the injection of up to 1 $\mu$L on a single capillary arrangement (Locke, S. J., Thibault, P., *Anal. Chem.*, 66 6436 (1994)). On-line trace enrichment can also be obtained by loading large volumes of sample using microcolumns containing adsorptive media, followed by elution or electromigration onto a CE column. A review of different chromatographic preconcentrators has been presented recently (Tomlinson, A. J., Guzman, N. A., Naylor, S., *J. Cap. Elect.*, 6, 2247 (1995)). These methods provide satisfactory means to overcome many detection limit problems.

Capillary Electrophoresis is a well established method and provides a number of separation formats thus giving flexibility for the analysis of different biomolecules. It is well suited as a sample introduction device to a mass spectrometer (Banks, J. F., Recent Advances in Capillary Electrophoresis/Electrospray/Mass Spectrometry. *Electrophoresis*, 18, 1997; and Cai, J. and Henion, J. Capillary Electrophoresis—Mass Spectrometry.*J. Of Chromatography A.*, 703, 1995) At the most recent High Performance Capillary Electrophoresis Conference in Orlando Fla., several research groups reported on their efforts to directly interface microfluidic devices to mass spectrometers (Ramsey, R. S. And Ramsey, J. M. New Developments in Microchip ESI Mass Spectrometry; Figeys, D. And Aebersold, R. Microfabricated Devices Coupled to an Ion Trap Mass Spectrometer for the Identification of Proteins; and Liu, H., Foret, F., Zhang, B., Felten, C., Jedrzejewski, P. And Karger, B. L. Development of Microfluidic Devices for High Throughput ESI/MS). These groups have demonstrated that it is possible to obtain an electrospray directly from the microfluidic device, but they did not demonstrate high efficiency separations. The inventors' experience with electrospray directly from the edge of a device, as in these other proposals, has shown that the droplet formed on the face of the device is sufficiently large that high efficiency separations are not possible due to the large mixing volume.

The effect of dead volumes is to distort the peak shape and increase band broadening. The maximum separation efficiency that can be observed with a microfluidic CE system joined to a capillary is limited by four principal sources of band broadening, namely longitudinal diffusion and effects of both injection and detection volume as well as any additional dead volumes.

One proposal has demonstrated reasonable separations with a device that included a pneumatic nebulizer (Foret, F., Liu, H., Zhang, B. and Karger, B. L., Single and Multiple Channel Microdevices for Microanalysis by ESI/MS. HPCE, Orlando, Fla., Feb. 1–5, 1998).

This still relies on forming an electrospray plume from the edge of the device, but combines this with a pneumatic or gaseous flow to improve nebulization of the emerging droplet, thereby reducing the droplet size and assisting in volatilization. A built in sprayer on the end of the chip is apparently simple and advantageous. However, it is believed that this can never give the same performance as a tapered capillary tip. Such a capillary tip provides a smaller droplet size, thus less dead volume, and less band broadening. The length of the capillary can be changed to meet changing resolution needs since separation continues in the capillary. These combined devices would be able to exploit commercial micro electrospray interfaces, with independent control over the electrospray operating parameters.

The literature has reported several methods used to join capillaries to microfluidic devices but to date they have shortcomings. Figeys et al. have constructed a butt joint to the edge of the chip with the use of a piece of Teflon tubing glued to the edge of the device as a guide sleeve and mooring point for the capillary. The capillary was used as an electroosmotic pump for the introduction of protein digests to a MS device (Figeys, D., Ning, Y. And Aebersold, R., *Anal. Chem.*, 69, 1997, p. 3153–3160). This article gives information regarding the dead volume of the connection. It also acknowledged the presence of contamination that may have been due to the epoxy used to glue the capillary in position. This method also requires that the capillary and the channel be aligned to within a few microns and held in position by the glue, a difficult task at best. This type of connection has the additional shortcoming that it is not possible to directly examine the joint for the presence of debris, glue or dead volume. These problems render this joining technique impractical for most applications.

With silicon it is possible to form a connection with minimal dead volume. This was demonstrated by van der Moolen et al (van der Moolen, J. N., Poppe, H. And Smit, H. C., *Anal Chem.*, 69, 1997, P. 4220–4225). The SEM images of the interface presented in their article showed a tight connection with no apparent dead volume. The device was intended for correlation CE and no investigations were made for presence of band broadening introduced from the joint. Furthermore, the silicon device was used as an injector and performed the separation on the capillary. Unfortunately it is not possible to chemically etch deep structures into glass while retaining flat surfaces suitable for joining to a capillary so that the silicon procedure used by Moolen is inappropriate for glass. The problem with silicon devices is their inability to sustain the high electric fields that glass devices exploit for rapid separations. Consequently, a method to make low dead volume connections to glass devices is still needed.

SUMMARY OF THE INVENTION

Instrumental modifications are required to improve the analytical performance of the CE-$\mu$ESMS interface in terms of ruggedness and speed of analysis. The present invention is based on the development of a compact and versatile, micromachined chip device to perform CE or other sample manipulation and then introduce the sample to a $\mu$ESMS system, giving a chip-CE-$\mu$ESMS hybrid system. The chips are thus an integral component of the electrospray ion source for the mass spectrometer, providing both sample treatment and ion source functions. The intent of the present invention is to develop a chip-ES interface which is easily manufactured, so that it can be made commercially at lower cost than current methods, and can increase utilization and sample throughput of rather powerful, but expensive instruments such as ESMS systems. This ES interface will be reusable, but readily replaced when required by the user.

Interfacing chips to $\mu$ESMS would greatly expand the potential of both CE and ESMS for biotechnological applications requiring faster analysis time, enhanced sensitivity and selectivity. On-chip separations will provide for sample clean-up and separation of components to prevent interference in the mass spectrum, with a substantial reduction in analysis time (less than 5 and typically under 2 minutes). Minute sample and reagent consumption with less solvent and salt introduction at the interface should also lead to increased performance and efficiency.

To address this need, the inventors have developed a method of connecting fused silica capillaries to microfluidic devices. Silica capillaries were chosen because electrophoretic separations begun on the device can continue on the capillary and silica is transparent over a wide wavelength range. The initial invention was to develop an interface to MS that exploits the common micro electrospray. The results of MS experiments are presented.

In accordance with the present invention, there is provided a method of joining a capillary tube to a microchip including at least one capillary channel that opens onto an edge surface of the microchip, the method comprising the steps of:

(1) drilling a flat-bottomed hole into the edge surface of the microchip, the hole being axially aligned with the channel; and (2) inserting an end of a capillary tube into the hole, abutting the capillary tube against the flat bottom, and bonding the capillary tube to the microchip;

so as to minimize dead volume between said capillary tube and said capillary channel.

The method can include bonding the capillary tube to the microchip with an adhesive substance. Advantageously, the adhesive substance is applied from the exterior, by capillary action and is permitted only to enter to the end of the capillary tube, without flowing substantially into an area between the end of the capillary tube and the capillary channel in the microchip.

Preferably, the method includes filling at least the end of the channel adjacent the edge surface of the microchip with an adhesive substance, to prevent substantial penetration of glass chips into the capillary channel. Conveniently, the substance is capable of being removed either by heating or by dissolution with a solvent.

It is preferred to provide the capillary with a tapered capillary tip, for use as an electrospray source for a mass spectrometer.

The hole can be drilled to a depth in the range of 2 to 5 times the diameter of the hole.

Advantageously, the method includes mounting the microchip in a drill press, providing a drill bit in the drill press, lowering the drill bit until it is close to the edge surface of the microchip, and viewing the drill bit through a magnifying means to ascertain that the drill bit is aligned with the capillary channel.

More preferably, the microchip device is mounted in a bracket, and the bracket is mounted on a Z axis translation stage, for movement in a horizontal X-Y plane, and the Z axis translation stage is adjusted to bring the capillary channel into alignment with the drill bit, for example by viewing the relative location of the drill bit to the capillary channel through a jeweller's loupe.

A combination device comprising:

(a) a microchip having at least one channel opening onto an edge surface thereon, and a hole extending from the edge surface into the microchip and axially aligned with the channel, the hole being flat-bottomed and having a larger cross-section than the cross-section of the capillary channel; and (b) a capillary tube mounted in the hole, abutting the flat bottom, and bonded to the microchip.

The capillary is advantageously bonded in position by an adhesive substance, which does not extend to an area between the end surface of the capillary tube and the flat bottom of the hole.

Another aspect of the present invention provides a method of joining a capillary tube to microchip including at least one capillary channel that opens onto an edge surface of the microchip, the method comprising the steps of:

(a) filling the end of the channel adjacent the edge surface of the microchip with a substantially solid substance having a substantially low melting point, to prevent substantial penetration of glass chips into the capillary channel;

(b) drilling a hole into the edge surface of the microchip, the hole being aligned with the capillary channel;

(c) removing the substantially solid substance from the capillary channel; and (d) inserting an end of a capillary tube into the hole and bonding the capillary tube to the microchip.

Another aspect of the present invention provides a method of joining a capillary tube to a microchip including at least one capillary channel that opens onto an edge surface of the microchip, the method comprising the steps of:

(a) providing a stream of fluid through the capillary channel such that a continuous flow of fluid out from the free end of the channel is produced;

(b) drilling a hole into the edge surface of the microchip, the hole being aligned with the capillary channel such that the flow of fluid flushes away drilling debris; and (c) inserting an end of a capillary tube into the hole and bonding the capillary tube to the microchip.

In yet another aspect of the present invention, this device is provided in combination with a mass spectrometer.

It is to be appreciated that this invention is not limited to application with mass spectrometers. More generally, the method is applicable to any aspect of microfluidic technology in which it is desired to connect a capillary tube to a microchip containing capillary channels. Such a device can be used to carry out a wide variety of different analytical and other techniques. The capillary tube itself need not necessarily have a free end, but could conceivably be connected at both ends to microfluidic chips, so as to provide an inter-connection between them. The capillary tube enables a channel of any desired length to be provided, and can enable a variety of different processing to be carried out, e.g. by irradiation of the tube and/or detection of substances travelling through the tube.

A chip-ESMS interface also offers other advantages. Microfabrication allows for multiple sample treatment manifolds on a single chip, so that multiplexing of sample introduction into a single MS is feasible, thereby increasing throughput. Also, regular supply of mass calibration standards is possible via the chip, giving improved mass accuracy. Finally, a variety of more complex sample treatments, such as on-chip digestion of proteins or DNA can further automate sample preparation and introduction in the $\mu$ESMS.

BRIEF DESCRIPTION OF THE DRAWING FIGURES

For a better understanding of the present invention and to show more clearly how it may be carried into affect, reference will now be made, by way of example, to the accompanying drawings which show a preferred embodiment of the present invention and in which:

FIG. 1 is a schematic perspective view of a microfluidic device and a capillary tube in accordance the present invention, with FIG. 1a showing a detail of the microfluidic device;

FIGS. 3a, 3b and 3c show sequentially steps in drilling a hole in the edge of the microfluidic device;

DESCRIPTION OF THE PREFERRED ENVIRONMENT

Figure 2:
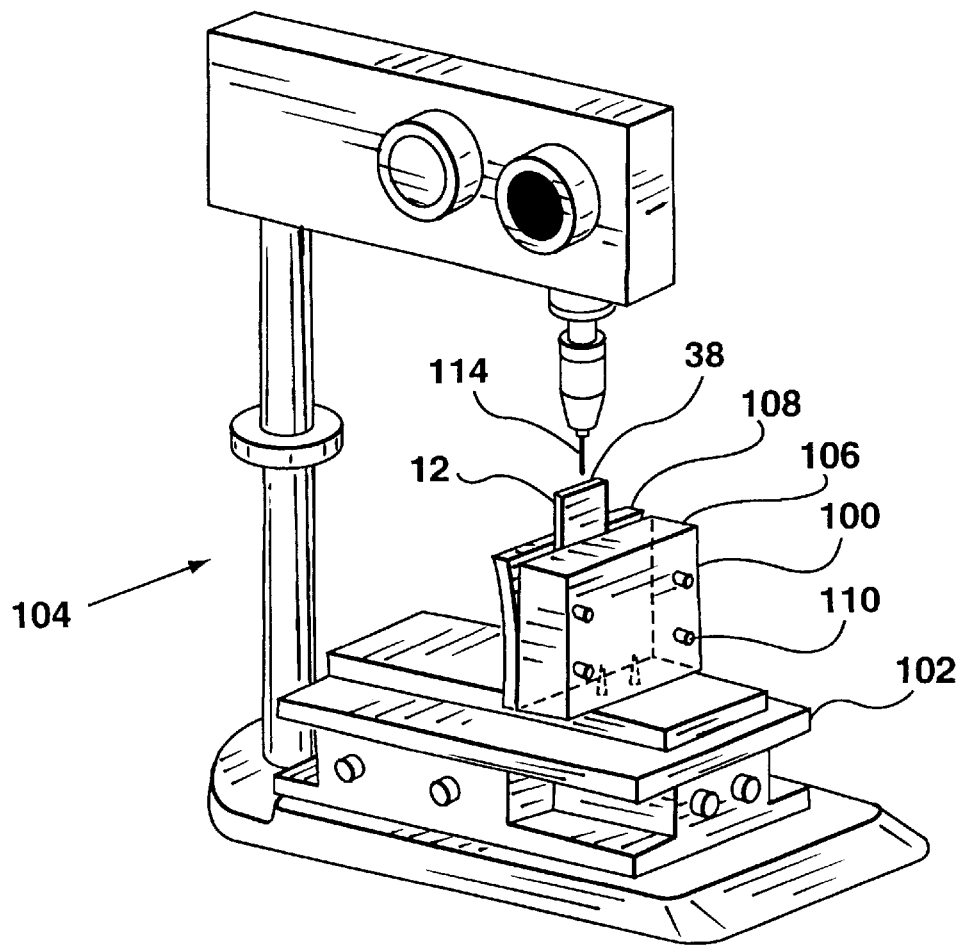
FIG. 2 shows a perspective view of a drilling press including a bracket in accordance with the present invention.

For the preferred embodiment of this invention, glass chips designed for interfacing directly to mass spectrometer were used, and these can have either a coaxial sheath flow arrangement or a sheathless interface. The chip can have a side channel at the end of the chip, forming a Y, that allows make up fluid flow and electrical control to assist the electrospray function. The glass chips were prepared using the techniques and procedures previously discussed in the literature. The glass chips or microfluidic devices were designed to have the separation channel exit the edge of the chip to form an electrospray and as such are well suited to the present experiments. FIG. 1 illustrates the overall layout of the device and the experimental setup.

FIG. 1 shows a combination device 10 comprising a microfluidic chip 12 and a capillary 14 connected thereto, in accordance with the present invention and as detailed below. Detectors 16 are indicated schematically, for detecting radiation from the chip 12 and the capillary 14. A counter electrode 18 is provided for test purposes, but its use would be replaced by a mass spectrometer. As indicated, in this preferred embodiment, the capillary 14 has a length, indicated at 20, of 5.3 cm. The end of the capillary, as indicated at 22, is spaced at 5 mm from the counter electrode 18.

The exact configuration of the microchip 12 is not critical to the present invention, and indeed any configuration of channels can be provided. Nonetheless, an exemplary channel configuration is detailed below.

The glass microchip 12 is formed from two layers. The channels are etched in one layer, and typically would have an approximately trapezoidal shape, or a cylindrical, oval or rectangular shape. A second glass sheet is then bonded to the top of the first sheet with the etched channels. The top sheet is usually formed with small holes, with a diameter of 1–2 mm, centered over the ends of the channels 26–36, so as to provide connections to reservoirs. Reservoirs can either be formed by bonding directly onto the top glass sheet or by otherwise forming a connection to the small holes.

A main microcapillary channel 22 extends from a junction with the capillary 14 indicated at 24. A buffer channel 26 is connected to the other end of the main micro channel 22. A sample line is provided at 28, and on the opposite side of the channel 22 there is a sample waste 30. A further channel 32 is provided, but this was not used for experiments detailed below. A floating reservoir line 36 is connected to the main channel 22, adjacent the junction 24.

Junctions between the channels 28, 30 and 32 and the main channel 22 are shown in detail in FIG. 1a. As shown, each of the channels 28, 30 and 32 forms a T-connection with the main channel 22, and they are all offset relative to one another. Between the channels 28 and 30, this creates a short section, indicated at 34 of the main channel 22. The configuration of the sample supply line and reservoir 28 and the sample waste 30, enables a portion of the sample to be flowed through to 30, and, once the supply of sample is cut off, there will be left a plug or fixed length of the sample in the section 34.

Reference will now be made to FIGS. 2 and 3, to describe the detailed manner in which the capillary tube 14 is joined to the microfluidic device or chip 12.

The glass chip 12 was first prepared by filling one end of the main or separation channel 22 with dyed Crystal Bond 509 (Aremco Products—Crystal Bond is a trade mark of Aremco Products) to aid visualization and prevent plugging the channel 22. One to two drops of black ink from a Staedtler Lumocolor permanent pen were mixed with approximately 1–2 ml of melted Crystal Bond to make the dyed Crystal Bond. Only the length of the separation channel 22 adjacent to the junction 24, where the device 12 was to be cut and drilled, was filled, since the material was quite viscous. The device 12 was placed on a hot plate (800 C.) and by applying vacuum on the side or reservoir channel 36, the desired segment of the main channel 22 was filled.

Crystal Bond was selected to fill the channel 22, over other possible options such as water and paraffin wax. It has a number of desirable attributes, namely: it is readily available; accepts dyes readily; it has a low melting point; forms free flowing chips reducing binding on the drill; and is largely insoluble in water yet readily soluble in acetone.

Figure 4:
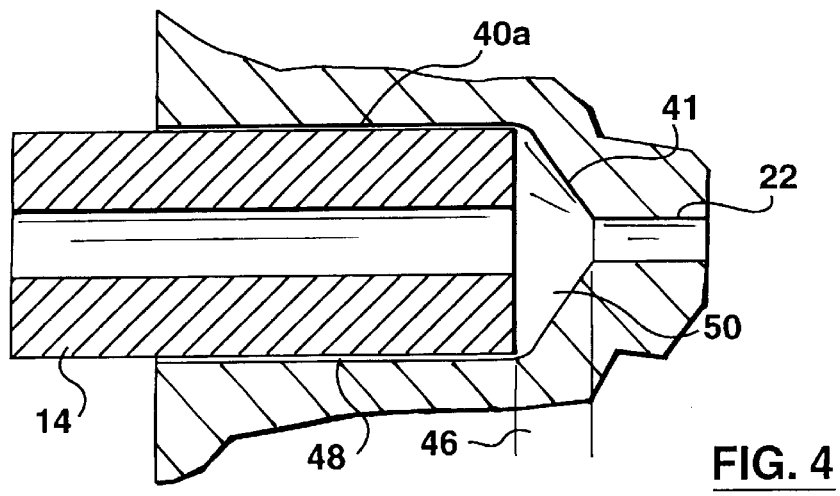
FIG. 4 is an image of a capillary inserted into a hole with a conical bottom, showing the dead volume.

Crystal Bond does have a disadvantage that prolonged exposure to water causes it to soften and expand. For this reason, the Crystal Bond is only allowed on the outside of the capillary and not to the area at the end of it, i.e. the dead volume 50 (FIG. 4). Other bonding materials can be used, but Crystal Bond does have the advantage that it allows a joint to be disassembled by gentle heating.

With the channel 22 filled with Crystal Bond, the device 12 was cut at the appropriate position perpendicular to the separation channel 22 with a diamond glass saw. The newly cut edge surface 38 was sanded smooth and flat with 220 grit and then 600 grit silicon carbide abrasive paper. This step facilitated locating the end of the separation channel and reduced the risk of the drill catching on the surface.

With reference to FIG. 2, the device was then clamped vertically to a bracket 100 mounted on a horizontal Z axis translation stage 102 (Newport, Irvine, Calif.) where the device is movable in a horizontal XY plane and the drill is movable vertically along the Z axis, with the main separation channel 22 held vertically and the end surface 38 on top.

As shown in FIG. 2, the translation stage 102 is mounted on the base of a drill press indicated generally at 104. The drill press 104 is a conventional, high quality drill press. The bracket 100 is secured, as by screws to the top of the translation stage 102. The bracket 100 includes a main body 106 and a clamping plate 108, and a number of screws 110 are provided, to provide a simple clamping action. The chip 12 can then be clamped between the main body 106 and the clamping plate 108, with its edge surface 38 at the top, as indicated. Then, in known manner, the drill bit, indicated at 114, and mounted in the chuck of the drill press 104 can be brought down vertically to engage the surface 38.

In accordance with the present invention, a flat bottomed hole was cut, forming the junction 24. This was carried out using 200 $\mu$ tungsten carbide drills and flat tipped drills which were purchased from Tycom (Mississauga, Ontario) and had nominal tolerances of +0 −8 μm. Alternatively flat tipped drills can be prepared manually by grinding the tip of the drill flat with a fine diamond wheel. A small jig was built to hold the drill bit and the wheel was rotated manually to avoid breaking the delicate drill. The manually flattened drill bits appear to produce better quality holes than the commercially prepared bits.

When drilling the hole, it was found necessary to use a high quality drill press 104 with no measurable runout. Such a press can produce holes with less potential for cracking of the wall of the hole and less drill bit breakage. The drill bit must follow the channel 22 within the chip 12; it was found that finer drills (200 mm) were better able to follow channel 22, having a nominal width of 45 microns, through the glass. It was also easier to center the drill bit. Due to their small diameter and brittle nature the glass powder must be removed from the drills.

The choice of capillaries compatible with the 200 micron size of drill was limited to 185 μm OD and 50 μm ID. Unfortunately this inside area of the capillary does not provide a very good match to the cross sectional area of the separation channel. The channel has a cross sectional area of approximately 450 μm$^2$ whereas the capillary has an area of 1960 μm$^2$ or about 4.4 times larger. Such large mismatch in areas can lead to unexpected band broadening due to inhomogeneous electric fields and distortions of the sample zone at the interface. The observed separation efficiency was about 95% of the predicted value for this volume mismatch, so the effect appears to be minor when the flat-bottomed connection is used.

Capillaries with a wider selection of ID are available in the 140 to 150 micron OD range but it was not possible to evaluate these capillaries. The 150 micron nominal OD drill bits that were tested in fact produced holes smaller than the available capillaries because of the relatively large negative tolerances on the drills. Larger drill bits (370 micron) produced holes suitable for (365 micron) capillaries which are available with a wide range of ID. These capillaries appear to have a larger dead volume because of the larger diameter and hence larger area that is not sealed with Crystal Bond. The larger capillaries were not evaluated because interfacing the device to the mass spectrometer, the impetus for this research, is more convenient with the smaller diameter capillaries.

The Z axis translation stage 100 was used to center the channel on the end of the drill bit 114. A 20X jewellers loupe and side illumination were used, while the drill tip 114 was about 0.2–0.5 mm above the surface of the chip, to facilitate alignment. Once the drill 114 was accurately centered it was turned on (4000 RPM) and lowered until the tip touched the edge surface 38 (FIG. 2), where it began removing glass. At this stage the drill 114 was raised and the face examined to ensure that the drill was on the center of the channel 22; if not, the chip 12 was removed, resanded and a new hole started.

If the hole was centered, a drop of water was placed on the surface of the device to help lubricate and cool the drill. The drill 114 was then lowered into the glass and allowed to bore approximately 1–2 drill diameters into the glass before it was raised. This process was repeated until a hole 40 of suitable depth (600–800 μm) was obtained (FIG. 3a). The face of the chip 12 was then cleaned with a paper towel to remove the glass powder produced during drilling. As detailed below both conventional conically tipped holes and flat bottomed holes were drilled for comparison purposes.

For the flat bottomed holes, the conventional conically tipped drill bit 114 was then replaced with the flat tipped drill. A new drop of water was placed on the device, the flat tipped drill was introduced and the bottom of the hole was flattened in one step (FIG. 3b), as indicated at 42. FIG. 3c illustrates that the bottom of the hole "fishtails" or widens out, if the flat tipped drill is forced to drill beyond the end of the hole left by the pointed or conical drill, as indicated at 66. The flat face of the drill bit is not capable of removing the glass so the lower wall of the hole is enlarged which results in a poor connection and possibly increased dead volume.

The glass debris was removed from the hole by using one of the two following techniques. If there were no air bubbles in the hole then the device or chip 12 was inverted in a beaker of water and the glass particles were allowed to settle out of the hole. This required a few hours. Alternatively a capillary (at least 25 μm smaller OD than the hole diameter) was used to flush the hole with filtered water (0.45 μm, Millipore). The chip was then placed on a hot plate and the Crystal Bond was melted and removed via the hole 40 at the end of the channel 22 with the aid of vacuum. The device 12 was removed, allowed to cool and the residues of the Crystal Bond were washed clean with reagent grade acetone (Caledon Laboratories Ltd., Georgetown, Ontario).

The end of the capillary 14 for connection at the junction 24 was prepared by sanding the end flat and square with 600 and 1200 grit silicon carbide paper, glass particles were flushed out with water. The capillary was glued into the device 12 by first placing the device 12 on a 10×10 cm scrap of glass to facilitate handling the hot assembly and then inserting the capillary tube 14 into the hole. The whole assembly was placed on a hot plate and allowed to heat to the Crystal Bond melting point (80° C.). A small amount of the Crystal Bond was applied onto the surface 38 face of the joint and allowed to wick into the hole 40 until it nearly reached the end of the capillary 14. The rate of flow was controlled by adjusting the temperature. The assembly was removed and cooled with forced air to freeze the Crystal Bond.

Figure 6:
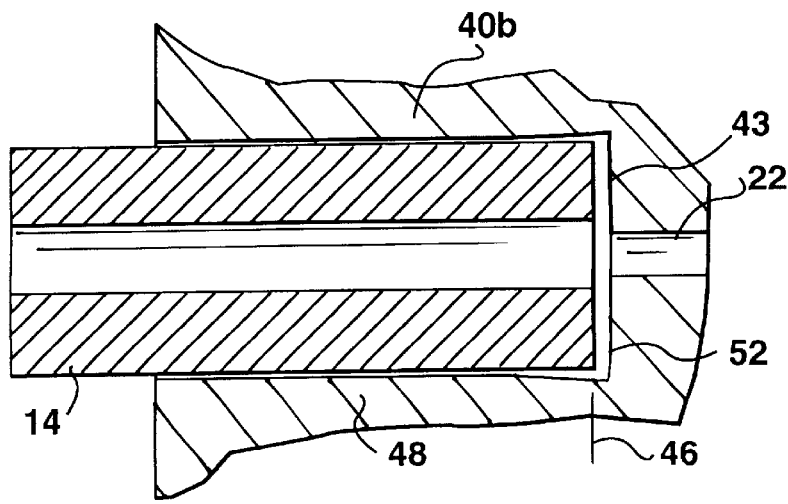
FIG. 6 is an image of a capillary inserted into a hole with a flat bottom.

Reference will now be made to FIGS. 4 and 6, which show the hole with a conical end, as drilled by a conventional drill and a flat-bottomed hole respectively. These holes in FIGS. 4 and 6 are indicated at 40a and 40b to distinguish them from one another and are also indicated as such in FIGS. 3a and 3b.

Referring first to FIG. 4, the hole 40a has a conical end surface indicated at 41. The capillary 14 is shown inserted into the hole 40a. The end plane of the capillary is indicated at 46, i.e. the capillary 14 has a square end surface 46. The Crystal Bond securing the capillary 14 in position is indicated at 48. As shown, the conical end face 41 prevents the capillary 14 reaching the end of the hole. Consequently, there is a relatively large dead volume 50, having a frusto-conical shape between the end plane 46 of the capillary 14 and the capillary channel 22. This dead volume 50, as shown, is relatively large compared to the dimensions of the capillary channels, and is a significant multiple of the length along any capillary.

Referring to FIG. 6, this shows a joint formed in accordance with the present invention. Here the hole 40b has a plane end face indicated at 43. Again, the capillary 14 is shown, secured in position with the Crystal Bond 48. It can now be seen that the end plane 46 with capillary 14 is very close to the bottom of the hole 43, so as to leave a relatively small dead volume 52. As explained below, this reduces band broadening due to dead volume effects.

The chip and capillary assembly was flushed with water, 0.1 M NaOH and then with the running buffer for 30 min. for the complete assembly or apparatus. Partially decomposed (due to age) 0.1 μM FITC labelled arginine diluted with buffer was used as a sample. Labelled arginine was prepared by mixing 7.63 mM arginine with 1.52 mM FITC (Sigma) before allowing the mixture to stand overnight at room temperature and stored at 40 C. 50 mM morpholine in deionized distilled water was used as a buffer with an unadjusted pH 9.5. Morpholine was chosen for this project because this buffer is suitable for MS detection of peptides.

A sample was injected (from sample line 30 in FIG. 1) by applying −1.5 kV at the sample waste 28 with 26, 30 and 36 grounded and the counter electrode 18 was left floating. With sample present at 34, separation was performed by applying −7 kV to the counter electrode 18, grounding the buffer reservoir 26, floating reservoir 36 and applying pushback voltages of approximately −550 V at 28 and 30, depending on liquid levels. During separation an electrospray formed at the tip of the capillary 14. A flat piece of copper was connected as a counter electrode with an electrospray gap 27 of 5 mm, as shown.

The channel 32, shown on the inset, is for a small volume injector, and was not used in this study and was left to float electrically.

Two devices, one where the hole was left with a conical bottom 40a from the pointed drill bit (FIG. 4) and another one with a flat bottomed hole 40b (FIG. 6) were used for the experiments and the experimental parameters are set out in Table 1. The difference in resolution caused by the different geometry of the two joints was evaluated by comparing the resulting electropherograms. Two separate 2 mW argon ion laser beams (448 nm) were focused to 40 μm diameter spots on the capillary 14 and the device, respectively. Fluorescence signals were collected during separation, one on the separation channel 22, 4.4 cm from the injector 34, 1 mm before the function 24 and the second on the capillary 4.9 cm after the junction, 4 mm from the tip of the 5.3 cm long capillary.

As detailed below in relation to FIGS. 8a and 8b, for electrospray operation an electrical connection needs to be made such that droplets emerging from the emitter are charged. This can be achieved by using the potential applied to the separation reservoir, 30 for example, to initiate both the separation and the ionization of analytes. As also detailed below, an electrospray emitter can be prepared by tapering one end of the fused silica capillary to a smaller diameter. Alternatively, electrospray contact can be made using a gold-coating capillary emitter, butted to the chip which also offers independent control of the electrospray voltage.

The effect of dead volumes is to distort the peak shape and increase band broadening for non-absorbing ions. The maximum separation efficiency within a microfluidic CE system is limited by longitudinal diffusion, the effects of both injection and detection volume as well as any additional dead volumes. A measure of the efficiency of a separation system is the ratio of the measured plate numbers to the maximum plate numbers predicted by theory. The number of plates predicted by theory can be expressed as $$N = L^2/\sigma^2 \quad (1)$$

where L is the length of the capillary and $\sigma^2$, the variance of the peak, is given by, $$\sigma^2 = 2D_i t + l_{inj}^2/12 + l_{det}^2/12 + \sigma_{dv}^2 \quad (2)$$

where $D_i$ is the diffusion coefficient of the analyte and t is analysis time, $l_{inj}$ is the length of the injected sample and $l_{det}$ is the detector spot size. The $\sigma_{dv}^2$ term represents the effect of the joint's dead volume, and is of an unknown form that depends on the geometric shape of the dead volume and the electric field. Using equations 1 and 2 we calculated the expected number of plates using a separation column (injector to detector distance) length of L=4.4 cm on the chip and 9.4 cm on the attached capillary. A $D_i$ value of 3.9×10⁶ cm²/s was used for all of the components in the labelled arginine sample. The detector length was 40 μm and the injector length 34 was 400 μm.

Figure 5:
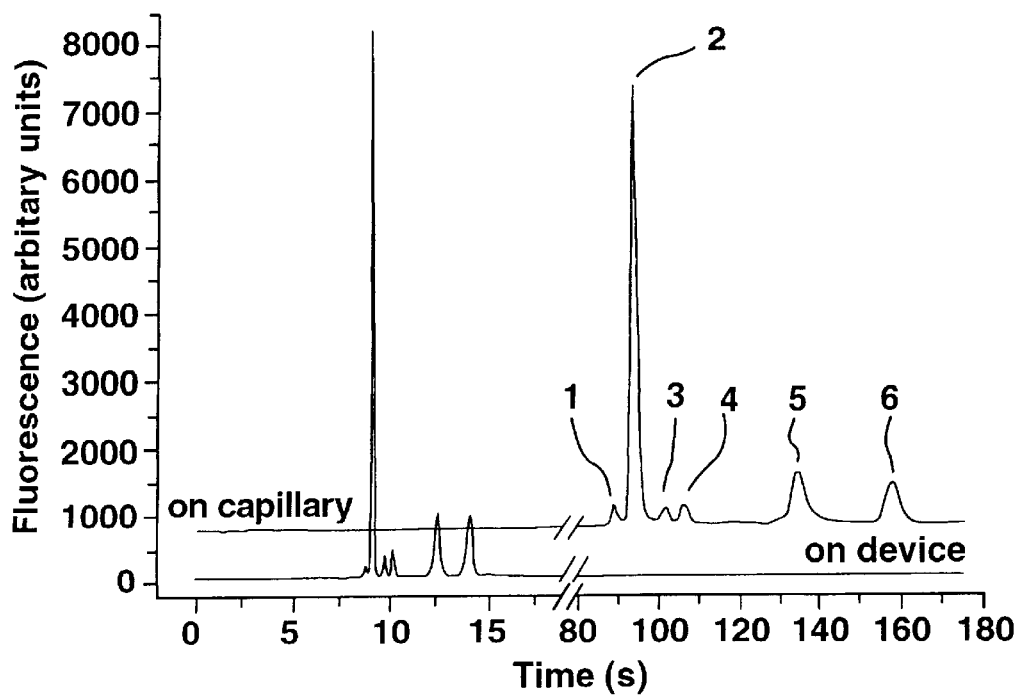
FIG. 5 shows electropherograms obtained using the combination device of FIG. 4.
Figure 7:
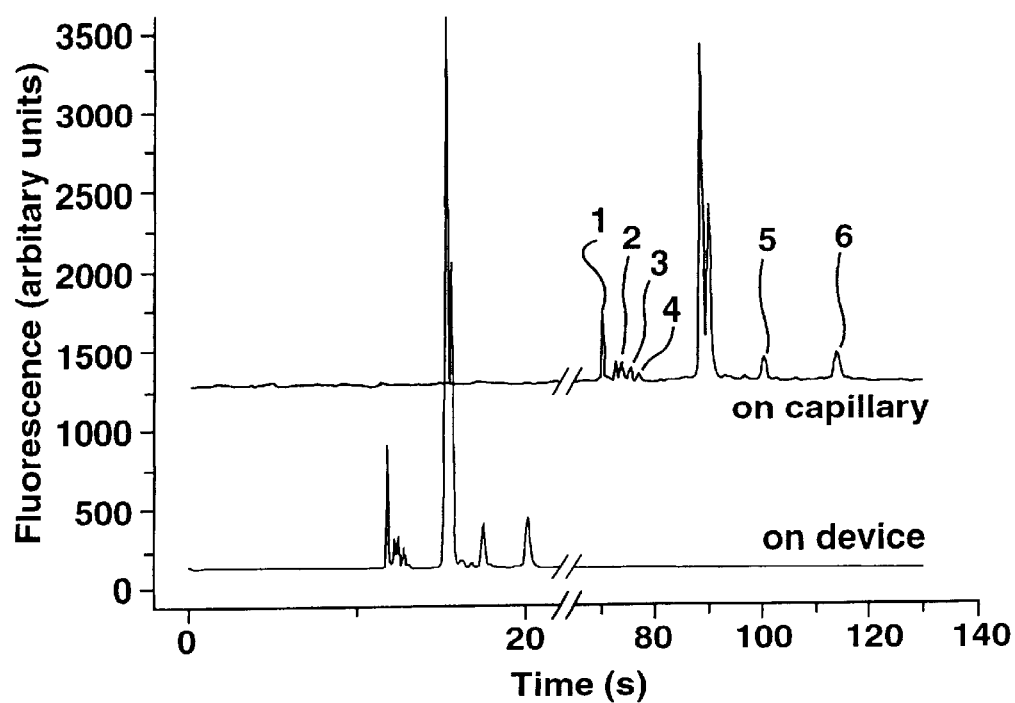
FIG. 7 shows electropherograms obtained using the combination device of FIG. 6.

The plate numbers were calculated from the well resolved peaks in FIGS. 5 and 7, the percentage ratio of the measured to calculated peak efficiencies are presented in Table 2. From FIG. 5 it is clear that the tapered bottom hole left by the pointed or conical drill bit (FIG. 4) introduces significant band broadening. For example, the plate numbers for Peak 2 went from 40,000 to 15,500 on going from the device to the capillary. As a result, this system only delivers about 12–17% of its theoretical efficiency. This should be contrasted with the data that was collected from the flat bottomed hole (FIG. 6) as shown in FIG. 7. In this case the plate numbers increased significantly from the device to the capillary and the observed efficiencies were in the range of 54–95% of the maximum. For example, the number of theoretical plates went from 47,000 to 112,000 and from 71,000 to 117,000 for peaks 1 and 3 respectively. Theory predicts that the increased length of separation on going from the chip to the capillary should also give increased total number of plates. The results presented in FIG. 7 agree with this and demonstrate that there is minimal dead volume at the joint between device and capillary.

Given this data, it is clear that drilling into the device represents a useful method for connecting microfluidic devices to common CE capillaries. The requirements for minimized dead volume in the flow path can be easily met by using tipped drills to create flat bottomed holes.

This technique for connecting capillaries could be used for attaching standard capillaries for a wide range of applications. For example simple injectors could be attached to capillaries to give standard CE instrumentation the high efficiencies and rapid sample introduction currently enjoyed only by complete microfluidic devices. Much of the current CE detector technology is based on UV absorption. With a capillary attached to the device it is possible to exploit UV absorption as a means of detection. Currently this is a difficult task for microfluidic devices unless constructed from fused silica and employing multi-reflection absorption cells.

The coupling of sample separation with mass spectrometry by means of electrospray ionization provides a powerful tool for rapid identification of analytes present in picogram levels in biological matrices, and structural characterization of complex biomolecules. Furthermore, ESMS has emerged as a sensitive technique in a number of applications including the sequencing of peptides comprising common or modified amino acids, and the analysis of short DNA oligomers. Microfluidic devices, which could easily be connected to commercial electrospray nebulizers by common CE columns applying the here described coupling technique, would greatly expand the potential of both CE and ESMS for biotechnological applications requiring faster analysis time, enhanced sensitivity and selectivity. The resulting on-chip separation and a wide variety of sample treatments, e.g. the on-chip digestion of proteins or DNA, would provide for sample clean-up and separation of components to prevent interference in the mass spectrum, with a substantial reduction in analysis time. Minute sample and reagent consumption, with less solvent and salt introduction at the MS interface should also lead to increased performance and efficiency.

For electrospray modes, the diameter of the tip is critically important to the performance of the device. Hence, the ability to change capillaries, and tip diameters, is particularly useful, since the type of tip of the capillary is quite fragile and susceptible to plugging and breakage.

Figure 8:
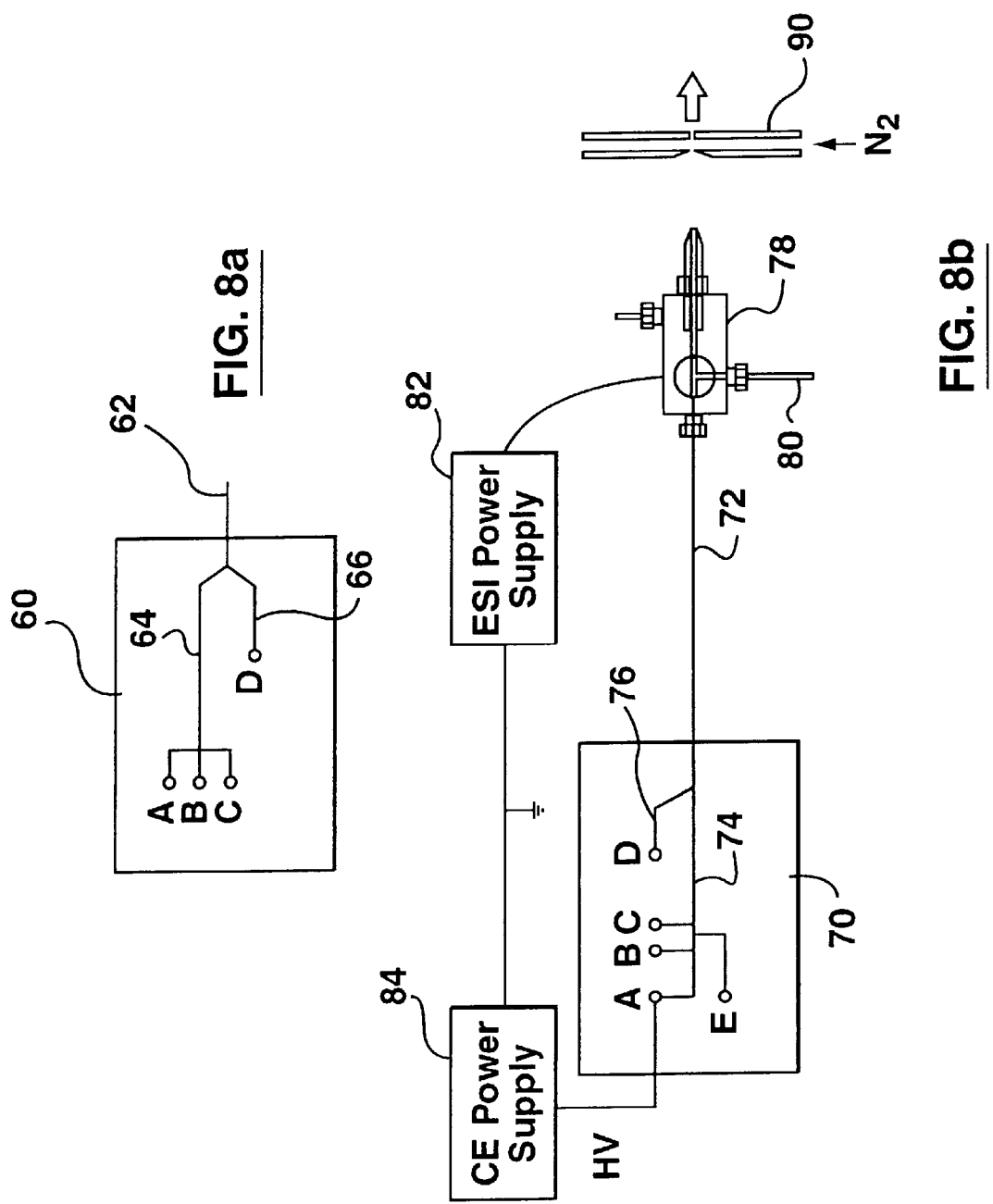
FIG. 8a shows a schematic view of a microfluidic device-ESMS coupled directly with a micro-electrospray emitter.
FIG. 8b shows a schematic view of a microfluidic device-ESMS interface using a coaxial sheath flow.

Referring now to FIG. 8a, there is shown, schematically, a microfluidic device 60 to which is attached a capillary tube 62, as described above. The microfluidic device 60 is provided with three wells, indicated at A, B and C, connected by short channels to a main channel 64. A side channel 66 is connected to an additional buffer D.

Here, the capillary tube 62 had a length of 1–5 cm, and a 180 micron outside diameter (50 micron inside diameter). It was prepared by tapering one end of a fused silica capillary tube to a diameter of approximately 50 microns o.d. or less.

For electrospray operation, an electrical connection needs to be made such that droplets emerging from the emitter are charged. This can be achieved by using the potential applied to the separation reservoir to initiate both the separation and the ionization of analytes (FIG. 8a).

A tapered tip can be provided by manually suspending a metal weight (15 g) from one end of the capillary and melting the fused silica with the flame from a microwelding torch (see K. P. Bateman, R. L. White, and P. Thibault, Rapid Commun. Mass Spectrom., 11, 307–315 (1997)) to taper the free end of the capillary tube to an inner diameter of 15 $\mu$m (50 $\mu$m o.d.). The other end of the capillary 62 is then inserted in the chip 60 as described earlier.

In use, a solution to be tested was supplied at well A in FIG. 7a. Typically, well B contains the separation buffer, and well C is the sample injection waste reservoir. A voltage applied between wells A and C creates a sample volume at the intersection of the channels. This plug is then driven towards the electrospray tip with a voltage applied between well B and the mass spectrometer. During the latter step a voltage can occasionally be applied to well D to assist the electrospray step. Typically voltages are in the range of 200 to 15,000 V on the chips, although 30,000 V has been demonstrated. Linear flow velocities of 0.01 to 15 mm/s can be achieved with these potentials. In order to improve the stability of the electrospray, an additional buffer solution was pumped from well D to increase the flow rate. The buffer solution was applied from the side channel (well D) with a flow rate of 50 nL/min. Also, a positive potential of the order of 5 kV was applied to well B to effect for both separation and analyte ionization. The configuration of the chip design required that the flow from the side channel 66 be set to 150 nL/min or lower. Increase of flow rate above 150 nL/min resulted in improved signal stability, though the sensitivity was reduced as a result of peak broadening and counter flow during the electrophoresis separation. Alternatively, electrospray contact can be made using a gold-coated emitter butted to the chip which also offers independent control of the electrospray voltage (see K. P. Bateman, R. L. White, and P. Thibault, Rapid Commun. Mass Spectrom., 11, 307–315 (1997)).

Reference will now be made to FIG. 8b which shows an alternative arrangement. The microchip is indicated at 70 and the capillary tube at 72. As for FIG. 8a, wells on the microchip are indicated A, B and C and are connected to a main channel 74. A side channel 76 is connected to a well D and an additional well E is provided. Here, the capillary tube, a fused silica transfer line 72, was generally longer and had a length of the order of 10–15 cm, with a 180 micron outside diameter and 50 micron inside diameter. It is connected to a T connector 78 including an inlet 80 for a sheath liquid. The sheath liquid flows in the inter-space between the CE column and the electrospray tip or needle at the tip of the connector 78 (see reference J. F. Kelly, S. J. Locke, L. Ramaley, P. Thibault, J. Cromatogr. A, 720, 409–427 (1996)). This approach provides an independent means of modifying the composition of the electrospray buffer for enhanced sensitivity, while simultaneously maintaining continuity of the voltage gradient across the CE capillary.

An ESI power supply 82 is connected between ground and the T connector 78. A CE power supply 84 is connected between ground and the well A as indicated from which to provide a potential for capillary electrophoresis.

As indicated schematically at 90, the electrospray could be directed to the inlet of a quadrupole mass spectrometer having a nitrogen curtain gas at the inlet, in known manner. The spectrometer could be, for example, a PE/Sciex API 300 (supplied by the Sciex Division of MDS Inc., of Concord, Ontario, Canada).

Figure 9:
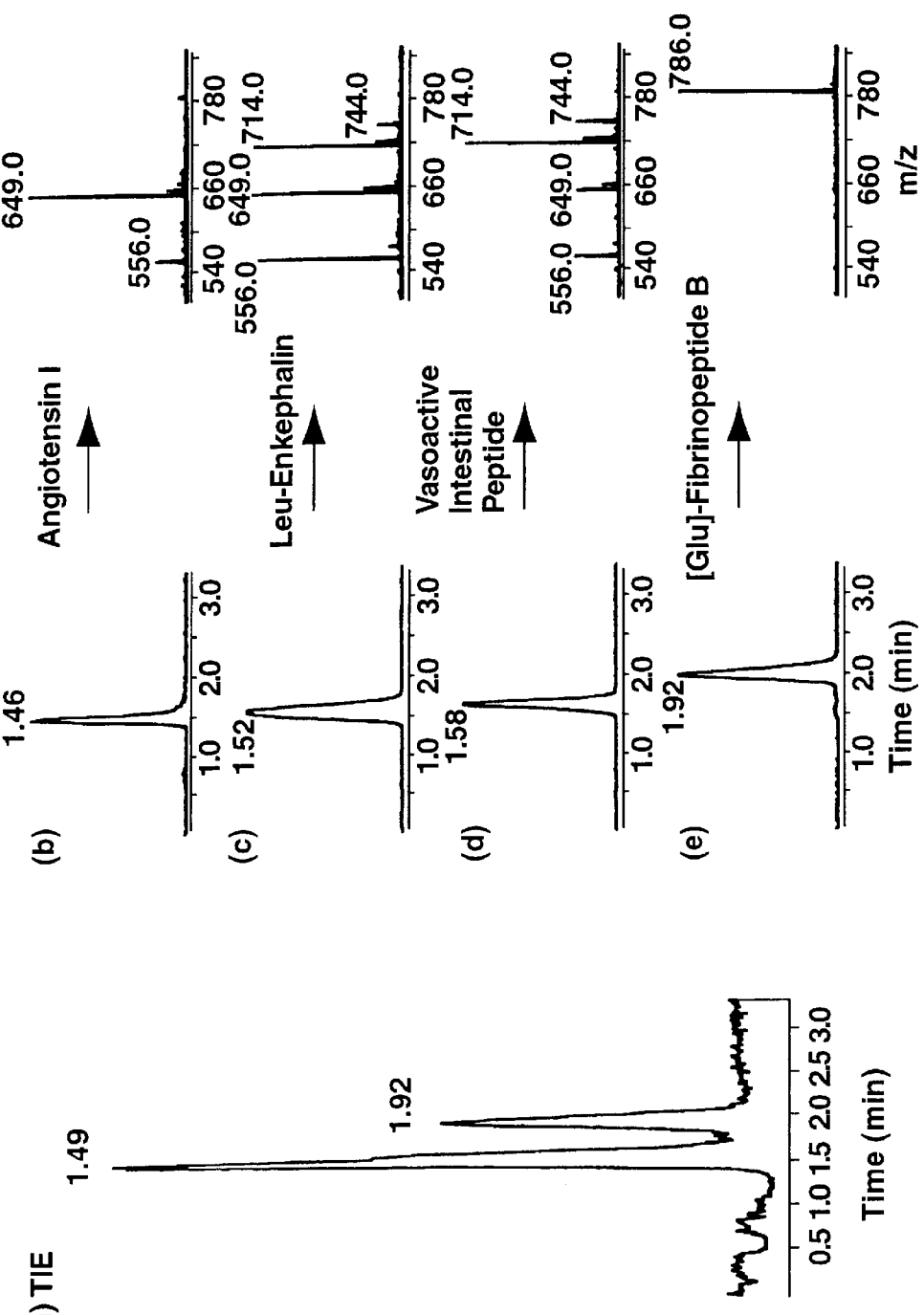
FIG. 9a shows an ion electropherogram from the microfluidic device-ESMS interface shown in FIG. 8a with extracted mass spectra for peaks highlighted in FIGS. 9b–9e.

An example of separation conducted using the chip-ESMS interface shown in FIG. 8a is presented in FIG. 9. The total ion electropherogram for m/z 500–800 (FIG. 9a) corresponds to the separation of a mixture of 9 peptides (injection of 64–180 fmol each). The main separation channel on the chip was 4 cm in length and neither the chip channels nor the electrospray emitter were coated. The peak width for individual components ranges from 12–20 sec. It is noteworthy that the separation efficiencies could be improved by increasing the length of the separation channel and reducing the tip of the electrospray emitter to smaller inner diameter. Extracted mass spectra taken for the peaks shown in FIG. 9(b)–9(e) are also presented on the right panels.

Figure 10:
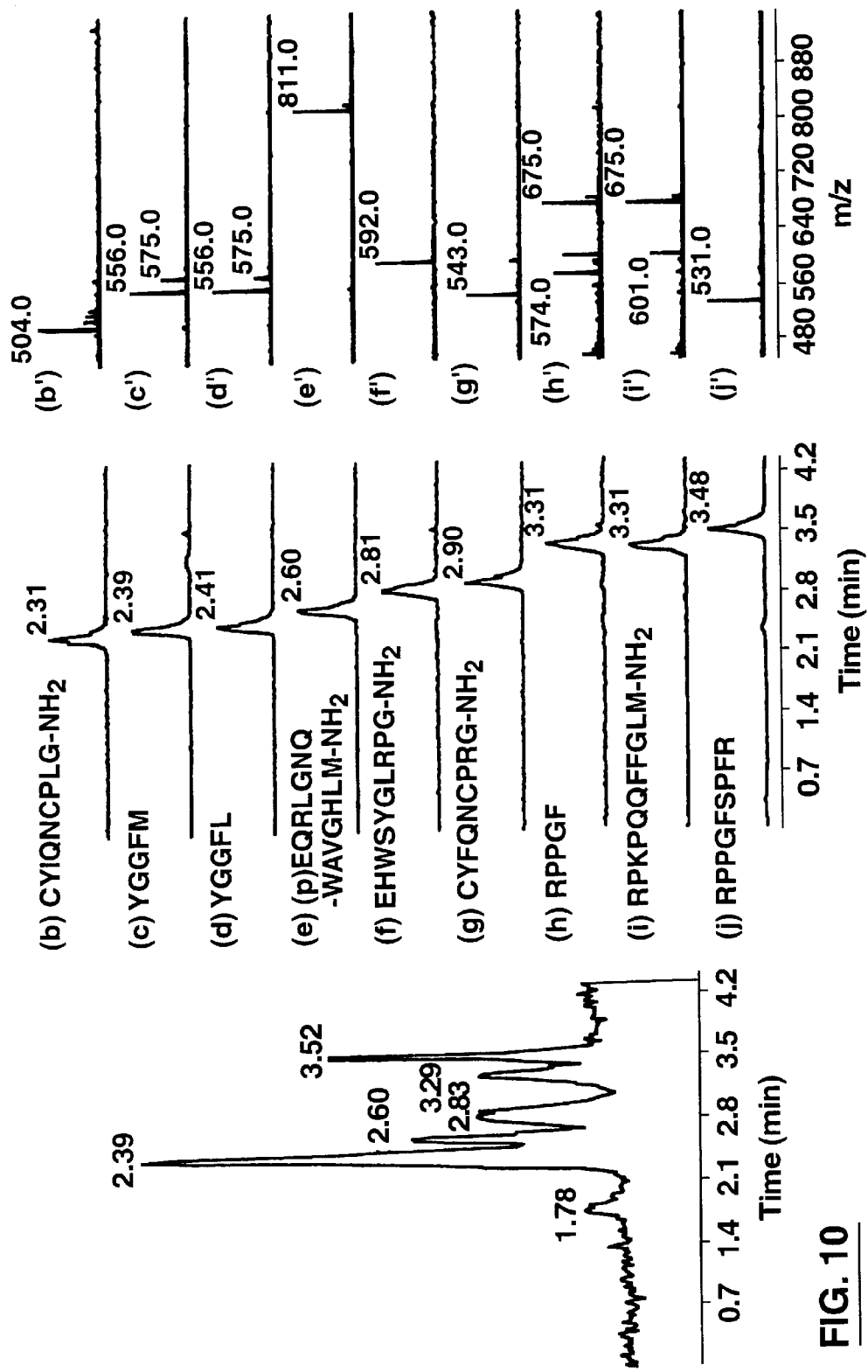
FIG. 10a shows an ion electropherogram from the microfluidic device-ESMS interface in FIG. 8b with extracted mass spectra for peaks highlighted in FIGS. 10b–10J.

The versatility of the chip-ESMS interface was also demonstrated for longer transfer line whereby this arrangement enables coupling to other types of mass spectrometric interfaces. An example of the chip-ESMS device using a 15 cm fused silica capillary coupled to a coaxial sheath flow interface is presented in FIG. 10 for the separation of the peptide mixture shown in FIG. 9. The coupling of the chip device via the co-axial sheath flow solvent delivery provides an independent means of optimizing the electrospray voltage or adding organic solvent to facilitate desolvation of the analyte. In this case both the chip of the capillary were coated with an amine reagent referred to as BCQ (see K. P. Bateman, R. L. White, and P. Thibault, Rapid Commun. Mass Spectrom., 11, 307–315 (1997)) which not only prevents analyte absorption on the inner walls of the chip and capillary but enables the use of acidic separation buffers. FIG. 10a shows the total ion electropherogram for the full scan analysis (m/z 400–900) of a mixture of 9 peptides each at 10 $\mu$g/mL. The ion electropherogram for the multiply-charged ions of each peptide are shown in FIGS. 10(b)–10(i). The mass spectrum for each peptide is dominated by singly and/or doubly protonated molecules of the corresponding peptides (peptides are designated in FIGS. 10(b)–10(j) using the single letter amino acid).

Figure 11:
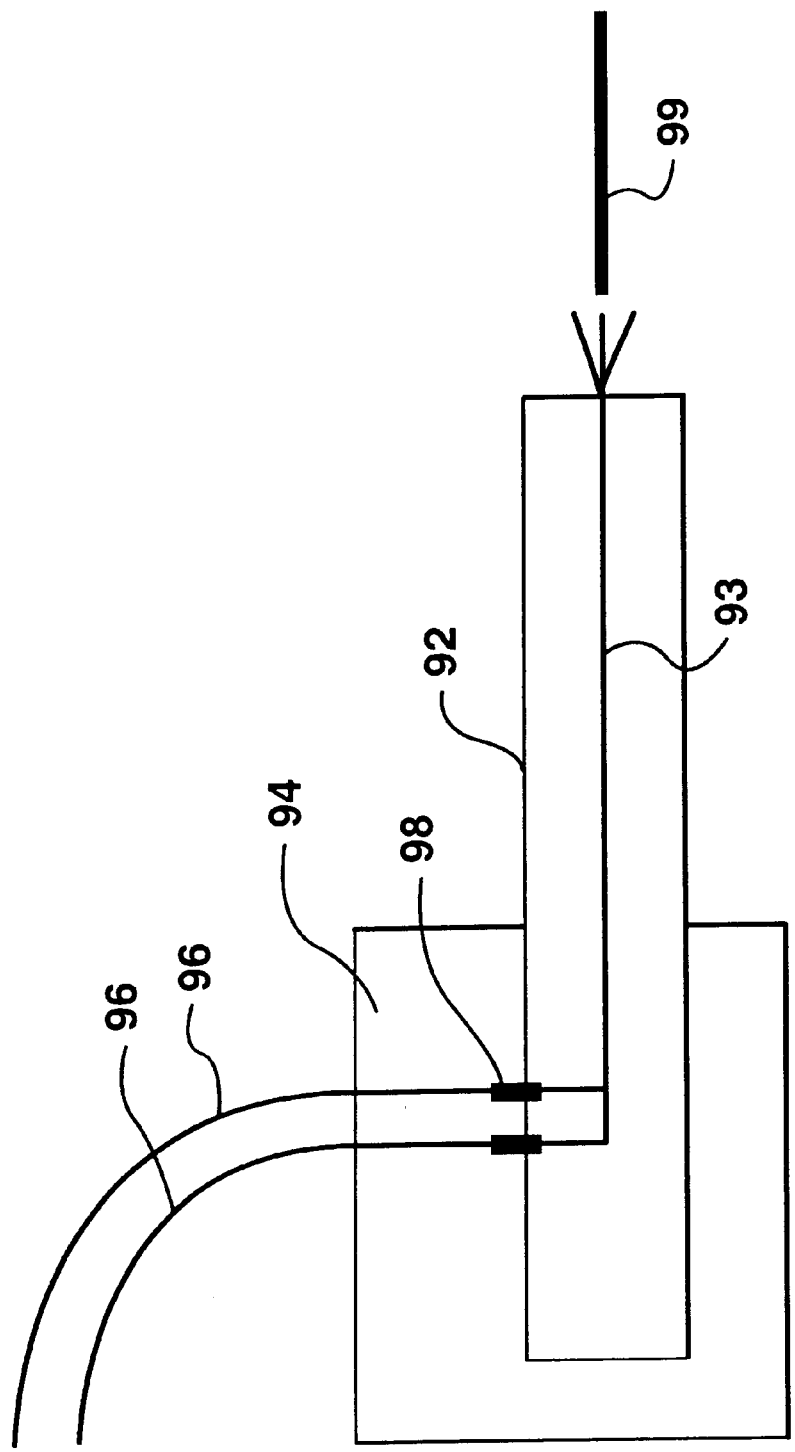
FIG. 11 shows schematically an apparatus for an alternative method of drilling a hole in the edge of a microfluidic device.

Reference is now made to FIG. 11, which shows an alternative apparatus and method for drilling a hole in a microchip device. Here, the microchip device is indicated at 92, and is shown held in a clamp 94. Separate tubes 96 are connected to a pump (not shown) and are sealed by O rings 99 to the microchip device 92. A drill bit 98 is brought up against an end of a channel 93 within the microchip 92, as indicated.

Here, a steady stream of water or other fluid is supplied through the tubes 96 from the pump, connected to the various wells or inlets to the channel 93. This produces a continuous flow of fluid out from the free end of the channel 93, as indicated in FIG. 11. Then, as the drill bit 98 is brought up against the channel, to drill a hole, the flow of fluid flushes away chippings, ground glass particles and the like.

It was found that this technique prevented plugging of the exit channel, but did not always prevent the trapping of some particles within the channels on the chip, particularly the channels on the chip with less than a 100 micron diameter and 20 micron depth. In general, it is expected that this technique would be better suited to larger size channels, where there is less likelihood of particles becoming trapped and a larger flow rate of flushing fluid can be maintained.

We claim:

1. A method of joining a capillary tube to a microchip including at least one capillary channel that opens onto an edge surface at the microchip, the method comprising the steps of:

(1) drilling a flat-bottomed hole into the edge surface of the microchip with a conically tipped drill bit, to form a hole with a conical bottom, and removing the conical end face of the hole with a flat tipped drill bit having the same diameter as the first mentioned drill bit, the hole being axially aligned with the channel; and (2) inserting an end of a capillary tube into the hole, abutting the capillary tube against the flat bottom, said capillary tube also being axially aligned with the channel, and bonding the capillary tube to the microchip;

so as to minimize dead volume between said capillary tube and said capillary channel.

2. A method as claimed in claim 1, which includes bonding the capillary tube to the microchip with an adhesive substance.

3. A method as claimed in claim 2, wherein the adhesive substance is applied from the exterior, by capillary action and is permitted only to enter to the end of the capillary tube, without flowing substantially into an area between the end of the capillary tube and the capillary channel in the microchip.

4. A method as claimed in claim 1, which includes providing the capillary with a tapered capillary tip, for use as an electrospray source for a mass spectrometer.

5. A method as claimed in claimed 1, which includes providing a flow of flushing fluid through the channel, to at least reduce penetration of particles into the channel.

6. A method as claimed in claim 1, wherein the method includes drilling the hole to a depth in the range of 0.9 to 10 times the diameter of the hole.

7. A method as claimed in claim 6, wherein the method includes drilling the hole to a depth in the range of 2 to 5 times the diameter of the hole.

8. A method as claimed in claim 6, which includes drilling the hole with a diameter in the range of 100 microns to one millimetre.

9. A method as claimed in claim 8, which includes drilling the hole with a diameter which is one of 150 microns, 200 microns and 360 microns.

10. A method as in claim 1, which includes mounting the microchip device in a bracket, and mounting the bracket on a horizontal Z axis translation stage, for movement in a plane perpendicular to the Z axis, and adjusting the translation stage to bring the capillary channel into alignment with the drill bit.

11. A method as claimed in claim 10, which includes viewing the relative location of the drill bit to the capillary channel through a jeweller's loupe.

12. A method as claimed in claim 11, which includes, after determining alignment of the drill bit by visual inspection, engaging the drill bit with the edge surface to begin removing glass, raising the drill bit and examining the edge surface to confirm correct location of the drill bit.

13. A method as claimed in claim 12, which includes, if the drill is incorrectly located, removing the microchip device, sanding the edge surface, mounting the microchip device again in the translation stage and repeating the steps of visually aligning the drill bit and checking to confirm correct location of the drill bit.

14. A method as claimed in claim 12, which includes providing water as a lubricating fluid.

15. A method as claimed in claim 12, which includes drilling the hole in a number of successive steps, each step comprising extending the depth of the hole in the range 1 to 2 times the diameter of the drill bit, and removing the drill bit out of the hole after each step, to ensure discharge of powder created by drilling.

* * * * *